United States Patent [19]
Sayles

[11] Patent Number: 5,501,837
[45] Date of Patent: Mar. 26, 1996

[54] ONE-STEP TEST DEVICE

[76] Inventor: Philip W. Sayles, 172 Sycamore St., Watertown, Mass. 02172

[21] Appl. No.: 497,539

[22] Filed: Jun. 30, 1995

Related U.S. Application Data

[63] Continuation-in-part of Ser. No. 275,256, Jul. 15, 1994, Pat. No. 5,429,804.
[51] Int. Cl.$^6$ .................................................. G01N 21/01
[52] U.S. Cl. ............................ 422/58; 422/61; 422/68.1; 422/102; 128/771; 604/404
[58] Field of Search ............................... 422/58, 61, 102, 422/68.1; 128/771; 604/318, 404; 436/165

[56] References Cited

U.S. PATENT DOCUMENTS

| | | | |
|---|---|---|---|
| 4,237,234 | 12/1980 | Meunier | 422/61 X |
| 4,473,530 | 9/1984 | Villa-Real | 422/61 X |
| 4,518,565 | 5/1985 | Boger et al. | 422/58 |
| 4,976,923 | 12/1990 | Lipsky et al. | 422/61 X |
| 5,069,878 | 12/1991 | Ehrenkranz | 422/61 |
| 5,119,830 | 6/1992 | Davis | 128/771 |
| 5,403,551 | 4/1995 | Galloway et al. | 422/58 |

*Primary Examiner*—Jeffrey R. Snay
*Attorney, Agent, or Firm*—William Nitkin

[57] ABSTRACT

A testing device having a lower cup for receipt of a fluid specimen and a cover lid containing a strip chamber having one or more reagent strips disposed therein and having a test chamber for each of the reagent strips, such test chamber receiving the end portion of the reagent strip, with each of the reagent strips having a color change testing area along its length. The cover lid is attachable to the cup in fluid-tight relationship with the device to be inverted for the fluid specimen to reach the reagent strips in the test chambers and react therewith, and for the device to be set upright for the reading of the color change testing areas through windows in the cover lid above the color change test areas.

7 Claims, 3 Drawing Sheets

ONE-STEP TEST DEVICE

This application is a continuation-in-part of my previous application for One-step Testing Device, Ser. No. 08/275,256 filed 07/15/94, now U.S. Pat. No. 5,429,804.

BACKGROUND OF THE INVENTION

1. Field of the Invention

The device of this invention resides in the area of structures for the conducting of chromatographic immunoassay testing of fluids on reagent-containing membrane strips and more particularly relates to a test container holding the fluid to be tested to accomplish one or a plurality of tests while the container is in a closed state.

2. Description of the Prior Art

Triage assay testing of bodily fluids is well known but has the serious disadvantage of requiring the tester to be exposed to contact with bodily fluids, such as urine, during the pipetting step. Such tests are slow, multi-step procedures which are difficult to carry out in hectic environments such as hospital emergency rooms.

In the prior art is U.S. Pat. No. 4,976,923 to Lipsky et al which patent discloses a specimen cup with a cover wherein the fluid to be tested is first placed in the specimen cup. The cover is positioned on the cup, and the closed cup is inverted so that the fluid can pass into apertures in the cover assembly where it reacts with a reagent therein to cause different color reactions which display the analytical characteristics of the fluid being tested. Such a specimen cup structure has great advantages in today's health environment where bodily fluids may contain dangerous viruses such as AIDS and the like. Health workers do not want to endanger their health by coming in direct physical contact with such fluids but still wish to perform necessary tests safely. In some cases the sealing of the fluids within such a specimen cup can be done by the person whose fluids are being tested. For example, in urine testing the subject whose urine is to be tested would urinate into the specimen cup and would then place the cover on the cup, sealing the urine in the cup. The lab technician performing the test need not open the cup or come in direct contact with the bodily fluids contained in the specimen cup. Thus a specimen cup which can be sealed during testing has a significant advantage over the open-cup fluid testing procedures of the past.

SUMMARY OF THE INVENTION

It is a goal of this invention to provide an improved closed specimen cup testing system utilizing a cover lid containing one or more reagent membrane strips for the efficient conducting of chromatographic immunoassay testing.

The structure of this invention in one embodiment provides for a cup, a cover lid, a strip chamber disposed within the cover lid having at least one test chamber along its periphery, and a plurality of reagent membrane strips, hereinafter called reagent strips, arrayed within the strip chamber, each extending into a separate test chamber. One end of each of the reagent strips extends through a notch formed in a side wall of its respective test chamber located at the periphery of the strip chamber and protrudes into a test area within the test chamber where such reagent strip's protruding end can come into contact with the fluid to be tested. After the cup is inverted, the fluid to be tested passes through apertures in a rotatable disk and through the open aperture in each test chamber to fill its interior. The disk is then rotated to cover the test chamber aperture, and the cup can be uprighted. The visible color change areas of the reagent strips are visible through elongated open windows formed thereover in the top surface of the cover lid.

In use, when the fluid specimen is placed within the specimen cup and the cover lid is affixed in fluid-tight relationship thereon such as by screw threads or other attachment means, the test chamber(s) are opened, as described below, and the specimen cup is inverted, allowing the fluid to be tested to enter each test chamber and come in contact with the end of each reagent strip which protrudes therein extending from the center of the strip chamber. Adjacent to the bottom of the strip chamber is a planar member such as a disk which is rotated by manually rotating a knob on the top of the cover lid which is attached to a shaft which operates the disk which has solid portions and apertures therein corresponding to the approximate size and position of the apertures in each test chamber. The knob is rotated until the solid portions cover the test chamber apertures, capturing a fixed amount of fluid in each. Each reagent strip is disposed in its own area of the strip chamber. The fluid is drawn along each reagent strip toward the center of the strip chamber by capillary action until the fluid comes to the bands of the chromatographic immunoassay test reagent where a color change can occur when each strip reacts with the fluid to perform the desired test. Very small amounts of the fluid sample are carried by capillary action from the test chamber along the length of the reagent strip. An open window in the top of the cover lid disposed immediately above its respective reagent strip allows the visible color change area of each reagent strip to be observed for color change reactions, and a label or indicia adjacent to each open window discloses the test each reagent strip is performing. Thus, if desired, multiple tests utilizing the same fluid specimen can be performed at one time. The testing device of this invention combines all the advantages of a closed container test system for fluids, such as urine and the like, and allows for efficient multiple tests to be performed simultaneously on specific quantities of the same fluid specimen.

DESCRIPTION OF THE PREFERRED EMBODIMENT(S)

Figure 1:
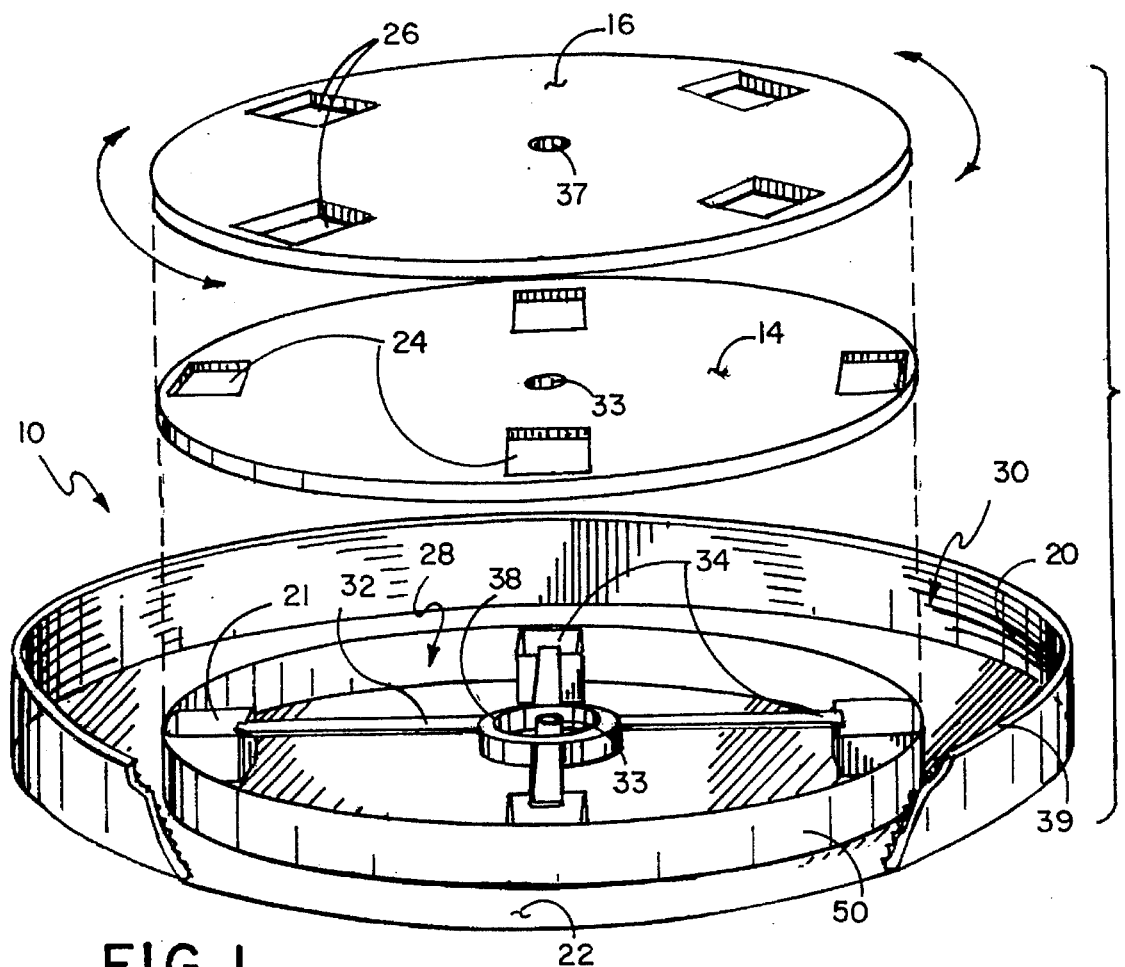
FIG. 1 illustrates a perspective exploded and inverted view of one embodiment of the cover lid of this invention showing its component parts.
Figure 6:
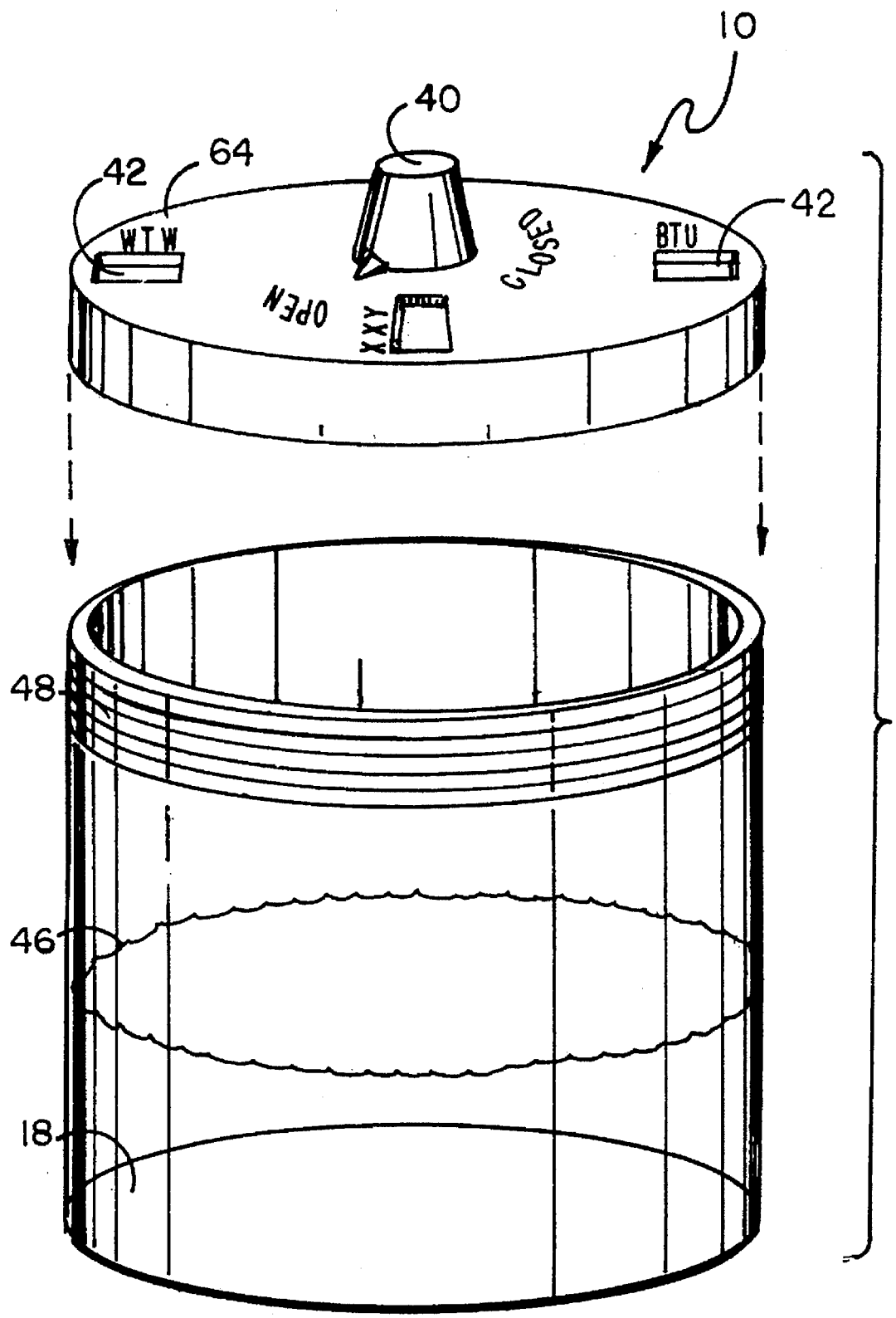
FIG. 6 illustrates a perspective view of the cover lid disposed on a cup having fluid therein.

FIG. 1 illustrates the cover lid of the fluid testing device of this invention in an inverted position. Not shown in this view is the cup containing the fluid to be tested which cup is well known. In use of the device of this invention the fluid to be tested is deposited in such cup. Threads are disposed at the outer top surface of the cup which threads interengage in fluid-tight relationship with mating threads 20 disposed on the inner side of cover lid side wall of cover lid 10 shown upside down in FIG. 1. Other means of fluid-tight attachment of the cover lid to the cup, such as friction-fit, can also be used as long as such means securely hold the cover lid onto the cup when the testing device is inverted for the fluid to enter the test chamber(s), as described below. Cover lid 10 has an open window 42, seen in FIG. 2, immediately above each visible color change area of each reagent strip 32. Indicia 64 to indicate the particular test being performed on the reagent strips, as seen in FIG. 6, can be printed on the cover lid's top surface next to open window 42. Also seen in FIG. 1 is strip chamber 28 having strip chamber side wall 50 permanently affixed to the bottom of cover lid 10, leaving a space 30 between strip chamber side wall 50 and cover lid side all 39 of cover lid 10 for receipt of the cup. Within strip chamber 28, around its periphery, are one or more test chambers 34. The size of each test chamber can vary depending on the test to be performed. At the bottom of each test chamber 34 in a wall thereof is defined a shallow, flat, elongated opening forming a notch 12 in which is positioned in mating relationship the protruding end 25 of reagent strip 32 which protruding end extends from the central area of strip chamber 28, totally filling notch 12 defined in test chamber 34.

Figure 2:
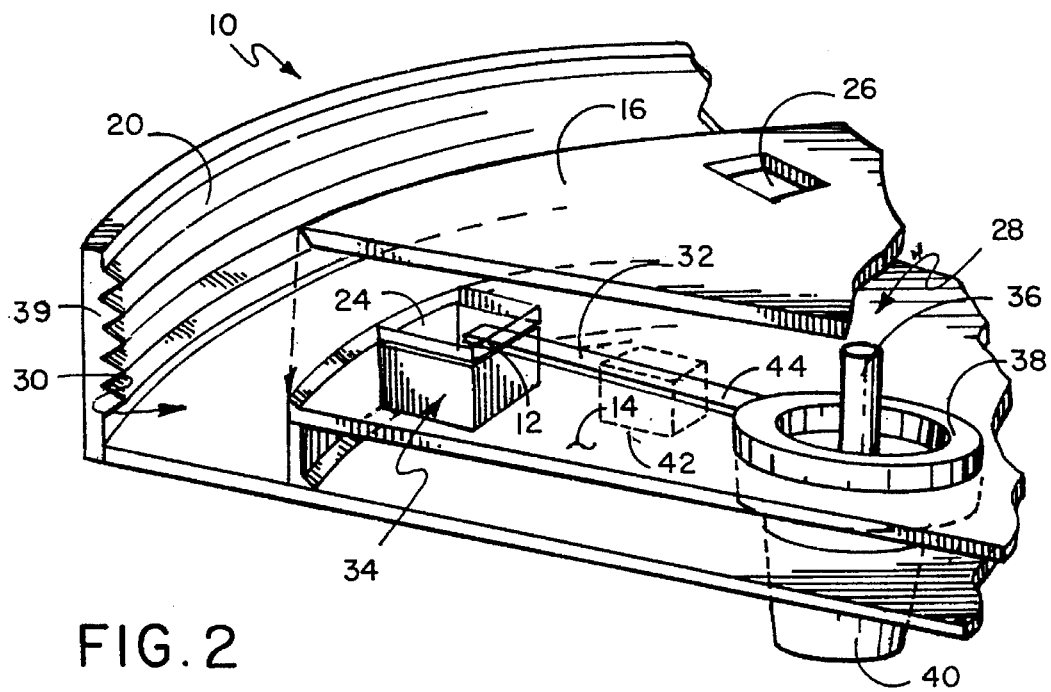
FIG. 2 illustrates a partial perspective sectional view of a portion of one embodiment of the cover lid showing a reagent strip extending within the strip chamber into a test chamber.
Figure 4:
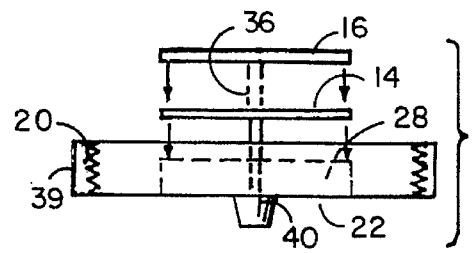
FIG. 4 illustrates a cross-sectional view of the embodiment of FIG. 1 showing the knob and shaft in place within the structure.

In FIG. 1 can be seen four test chambers 34 in a circular array within the periphery of circular strip chamber 28 with each reagent strip passing through notch 12 of its respective test chamber. Each test chamber can be of a predetermined size and have an open bottom 21 shown facing upwards in FIG. 1. With the exception of the open bottoms of the test chambers, strip chamber 28 can be sealed by bottom wall 14 attached onto strip chamber side wall 50. In the embodiment in FIG. 1 the strip chamber is circular, and the reagent strips are arrayed extending outward from an absorbent pad disposed in the central area of the strip chamber. In an alternate embodiment, as shown in FIG. 4 and described further below, the reagent strips can be arrayed parallel to one another in a rectangular strip chamber. Bottom wall 14 has an opening 22 disposed above each test chamber aperture 24 to allow the fluid to be tested to pass only within each test chamber and not within other portions of the strip chamber. Positioned below bottom wall 14, when the device is in its upright position, is a rotatable planar member such as disk 16 having a plurality of disk apertures 26 therein in corresponding size and position to mate over each test chamber aperture 24 and over the open bottom 21 of each test chamber. Disk 16, as seen in FIG. 2, is attached in a fluid-tight relationship against bottom wall 14 and can be rotated by central shaft 36 which passes through cover lid 10 which shaft is attached to rotatable knob 40 located on the top of cover lid 10. For clarity of illustration, shaft 36 is not illustrated in FIG. 1. Shaft apertures 33 receive shaft 36. The shaft can be attached to disk 16 at shaft attachment point 37. By rotating knob 40, disk 16 rotates either to align disk apertures 26 with test chamber apertures 24 or to misalign such apertures. When disk 16 is rotated to misalign the respective apertures, then each test chamber 34 is sealed closed by the body of disk 16. When the cover lid is placed on a cup containing fluid to be tested and inverted and knob 40 is rotated to align disk apertures 26 with test chamber apertures 24, then each test chamber will fill with the fluid being tested. The knob can then be rotated again, closing and sealing the fluid in each test chamber with a predetermined amount of fluid which is in contact with the protruding end 25 of each reagent strip extending through its respective notch in the test chamber. Since sufficient fluid must contact the protruding end of the reagent strip in each test chamber 34 to properly perform the desired tests, each test chamber can be of a size to accomplish each desired test.

FIG. 2 illustrates a portion of cover lid 10 showing protruding end 25 of reagent strip 32 passing through notch 12 into test chamber 34 covered by disk 16. In FIG. 2 fluid 46 has entered test chambers 34, and knob 40 has been rotated to misalign disk apertures 26 with test chamber apertures 24 and thus closing test chambers 34 and capturing fluid therein. The fluid from test chamber 34 travels along reagent strip 32 to the visible color change area 44 immediately under open window 42, when the device is in its upright position, where it can be seen from the top of cover lid 10. A plurality of notches can be defined in absorbent pad 38, each of a size to receive and hold the interior end portion of each reagent strip in mating relation thereto. Absorbent pad 38, being in contact with the interior end portions of each reagent strip, aids in drawing fluid from protruding ends 25 of reagent strips 32 along the lengths of the reagent strips by capillary action.

It should be noted that notch 12 in the side wall of each test chamber 28 and the corresponding notch in the absorbent pad can be completely filled by the two ends of a reagent strip so that no fluid directly flows out of the test chamber into the strip chamber. Thus the individual test chambers, each isolated by lack of fluid contact from its adjacent-positioned test chamber prevents any transference of any reagents from one reagent strip to the other. Absorbent pad 38, into which one end of the reagent strip extends or is in direct contact with, picks up and retains any excess fluid sample that may pass along the reagent strips and aids in the interior flow of the fluid to be tested along the length of each reagent strip.

Figure 3:
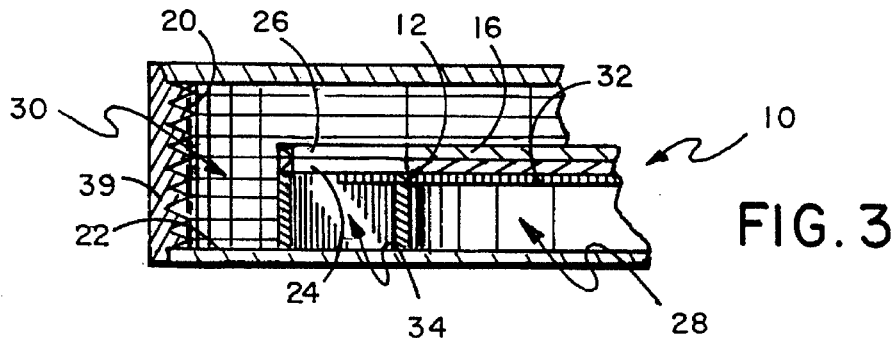
FIG. 3 illustrates a partial cross-sectional view of a portion of the cover lid showing the strip chamber, a reagent strip and a test chamber.

FIG. 3 illustrates a cross-sectional enlarged view of a portion of the inverted cover lid, better showing protruding end 25 of reagent strip 32 disposed in test chamber 34.

FIG. 4 illustrates a cross-sectional exploded view of the cover lid in an inverted position with bottom wall 14 and disk 16 separated from strip chamber 28 and showing the positioning of knob 40 and shaft 36 for rotating disk 16.

Figure 5:
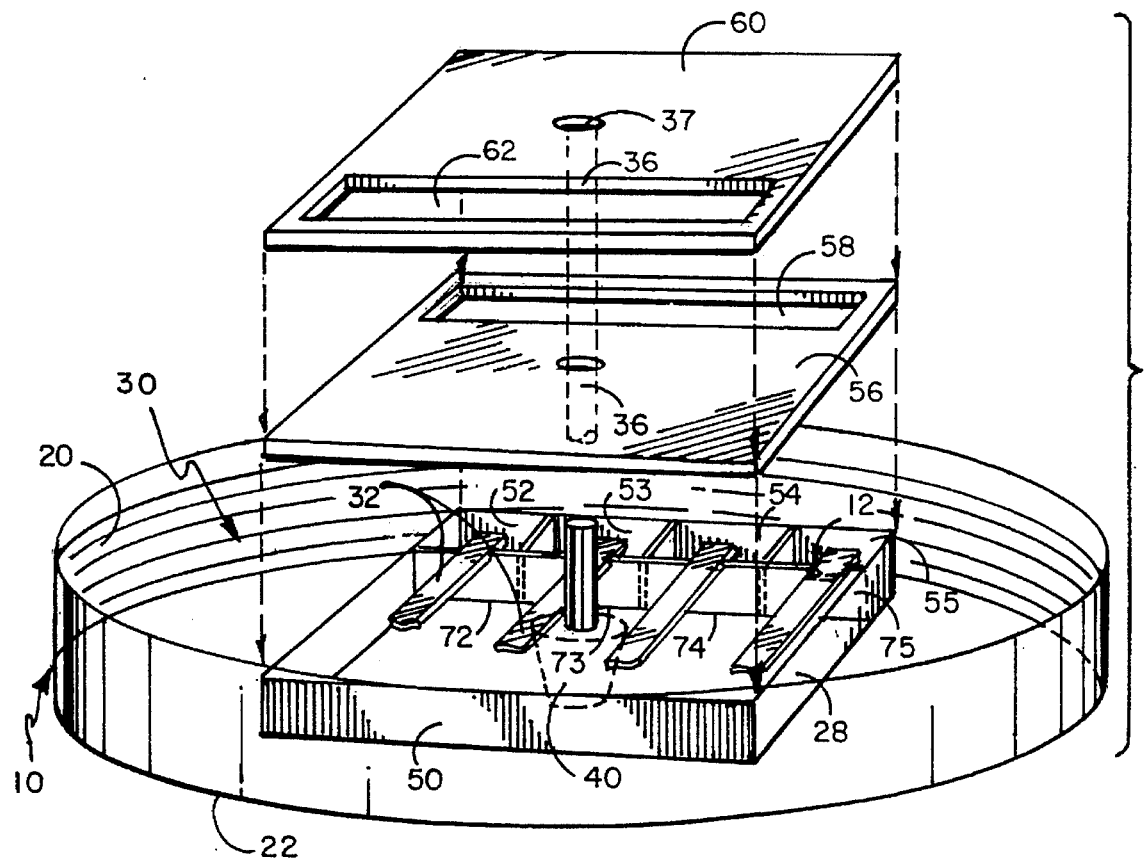
FIG. 5 illustrates an exploded perspective view of an alternate embodiment of the cover lid having reagent strips disposed parallel to one another within a rectangular strip chamber.

FIG. 5 illustrates a perspective view of an alternate embodiment of cover lid 10 shown in an inverted position, such embodiment having a rectangular strip chamber 28 with test chambers 72, 73, 74 and 75 therein arrayed adjacent to one another along one side thereof so that reagent strips 32 are disposed parallel to one another. Rectangular bottom wall 56 has a rectangular bottom wall aperture 58 defined therein that extends over the open test apertures 52, 53, 54 and 55, respectively, of test chambers 72, 73, 74 and 75. Rectangular cover 60 has a rectangular cover opening 62 therein corresponding to the size and shape of rectangular bottom wall aperture 58. When the cup having a rectangular strip chamber containing fluid is inverted and rectangular bottom wall 56 is rotated by manually rotating knob 40 connected to shaft 36 to align rectangular cover opening 62 with rectangular bottom wall aperture 58, the fluid will pass through test chamber apertures 52, 53, 54 and 55 and into, respectively, the interiors of test chambers 72, 73, 74 and 75 in a similar manner as described above. Not shown in this view are the open windows on the top surface of the cover lid through which the visible color change areas of the reagent strips can be viewed. For some tests the visible color change areas of the reagent strips can be read more easily and faster when the reagent strips are in parallel alignment with one another.

FIG. 6 illustrates a perspective view of the test device of this invention in an upright position showing cover lid 10 disposed on cup 18 containing fluid 46. Cup 18 is held in fluid-tight relationship to cover lid 10 by threads 20 on the cover lid mating with threads 48 on the cup. Also seen in FIG. 6 are open windows 42 on the top surface of cover lid 10. The colorimetric changes showing the test results can be observed through open window 42 with each reagent strip identified by indicia 64, as seen in FIG. 6, to indicate which test is being performed by the particular reagent strip that is located immediately adjacent to such indicia.

Although the present invention has been described with reference to particular embodiments, it will be apparent to those skilled in the art that variations and modifications can be substituted therefor without departing from the principles and spirit of the invention.

I claim:

1. An improved test device having a testing mode, said device for receipt of a fluid specimen to be tested, said test device having a cup with a cover lid, said cover lid able to be attached to said cup in fluid-tight relationship, further comprising:

at least one window defined in said cover lid, said cover lid having a central portion with a central portion aperture defined therein, a top, a bottom surface of said cover lid and a cover lid side wall;

a strip chamber having a central portion, a bottom wall having a bottom wall aperture defined therein, and a strip chamber side wall, said strip chamber side wall disposed in contact with said bottom surface of said cover lid disposed interior to and spaced away from said cover lid side wall defining a space therebetween, said space between said strip chamber and said cover lid side wall defining a space for receipt of said cup;

at least one test chamber having an interior, a bottom, a test chamber side wall and a test chamber aperture defined in said bottom of said test chamber, said test chamber positioned within said strip chamber and having a reagent strip receipt notch defined in said test chamber side wall;

means to open and close said test chamber aperture; and at least one reagent strip having a length, a first end portion and a second end portion, said reagent strip having a color change testing area disposed along its length, said reagent strip being substantially disposed in said strip chamber, said second end portion extending through said reagent strip receipt notch in said test chamber and into said interior of said test chamber, said device in its testing mode with a fluid specimen contained within said cup and said cover lid attached thereto, to be inverted, causing said fluid to flow into said interior of said test chamber, when said test chamber aperture is open, and to come in contact with said second end portion of said reagent strip, said fluid being carried along said reagent strip to said color change testing area to create a test result which test result can be viewed through said window in said cover lid.

2. The device of claim 1 having a plurality of test chambers and a corresponding number of reagent strips wherein said reagent strips are disposed extending radially outward from said central portion of said cover lid.

3. The device of claim 1 having a plurality of test chambers and a corresponding number of reagent strips wherein said reagent strips are disposed parallel to one another.

4. The device of claim 1 wherein said interior of said test chamber is of a size to contain a predetermined amount of fluid to be tested.

5. The device of claim 1 further including an absorbent pad adjacent to said first end portion of said reagent strip.

6. The device of claim 1 wherein said means to open and close said test chamber aperture further include:

said strip chamber bottom wall having a bottom wall aperture defined therein corresponding in shape, size and location of each of said test chamber aperture, said bottom wall aperture positioned over each test chamber aperture;

a rotatable planar member having at least one aperture defined therein corresponding in shape, size and location of said test chamber aperture; and means to rotate said planar member to alternately align said planar member aperture in said planar member with said test chamber aperture to allow fluid to enter said interior of said test chamber and to misalign said planar member aperture in said planar member with said test chamber aperture to cause portions of said planar member to cover over said test chamber aperture to capture said fluid within said interior of said test chamber.

7. The device of claim 6 wherein said means to rotate said planar member further includes:

a knob disposed above the top of said cover lid; and a rotatable shaft having a first end and a second end, said first end attached to said knob, said shaft passing through said central portion aperture of said central portion of said cover lid and through said bottom wall aperture of said bottom wall with said second end of said shaft attached to said planar member.

\* \* \* \* \*